United States Patent [19]

Kaczorowski et al.

[11] Patent Number: 5,776,734
[45] Date of Patent: Jul. 7, 1998

[54] DNA ENCODING THE β SUBUNIT OF A MAMMALIAN MAXI-K POTASSIUM CHANNEL

[75] Inventors: Gregory J. Kaczorowski; Maria L. Garcia; Reid J. Leonard; Owen B. McManus; Richard J. Swanson; Kimberly L. Folander, all of Rahway, N.J.

[73] Assignee: Merck & Co., Inc., Rahway, N.J.

[21] Appl. No.: 732,506

[22] PCT Filed: May 9, 1995

[86] PCT No.: PCT/US95/05768

§ 371 Date: Nov. 12, 1996

§ 102(e) Date: Nov. 12, 1996

[87] PCT Pub. No.: WO95/31543

PCT Pub. Date: Nov. 23, 1995

Related U.S. Application Data

[63] Continuation-in-part of Ser. No. 389,668, Feb. 16, 1995, Pat. No. 5,637,470, which is a continuation-in-part of Ser. No. 242,811, May 13, 1994, abandoned.

[51] Int. Cl.$^6$ ............... C12N 15/12; C07K 14/705
[52] U.S. Cl. ............... 435/69.1; 536/23.5; 435/320.1; 435/325; 435/252.3
[58] Field of Search ............... 536/23.5; 435/320.1, 435/325, 252.3, 69.1, 7.21, 29

[56] References Cited

U.S. PATENT DOCUMENTS

| | | |
|---|---|---|
| 4,960,867 | 10/1990 | Garcia et al. |
| 5,401,652 | 3/1995 | Sokol et al. |
| 5,637,470 | 6/1997 | Kaczorowski et al. ............... 435/7.21 |

OTHER PUBLICATIONS

Garcia–Calvo, M., et al., "Purification and Reconstitution of the High–conductance, Calcium–activated Potassium Channel from Tracheal Smooth Muscle", Chem., vol. 269(1), pp. 676–682, 1994.

Knaus, H.G., et al., "Subunit Composition of the High Conductance Calcium–activated Potassium Channel from Smooth Muscle, a Representative of the mSlo and slowpoke Family of Potassium Channels", J. Biol. Chem., vol. 269(6), pp. 3921–3924, 1994.

Lu, L., et al., "Ca2+–activated K+ Channels from Rabbit Kidney Medullary Thick Ascending Limb Cells Expressed in Xenopus Oocytes", J. Biol. Chem., vol. 265(27), pp. 16190–16205, 1990.

McManus, O.B., et al., "An Activator of Calcium–Dependent Potassium Channels Isolated from a Medicinal Herb", Biochemistry, vol. 32(24), pp. 6128–6133, 1993.

Gianagiacomo, K.M., et al., "Synthetic Charybdotoxin–Iberiotoxin Chimeric Peptides Define Toxin Binding Sites on Calcium–Activated and Voltage–Dependent Potassium Channels", Biochem., vol. 32, pp. 2362–2370, 1993.

Ashcroft, F.M., et al., "Expression of K Channels in Xenopus Laevis Oocytes Injected with Poly(A+) mRNA from the Insulin–secretimg Beta–cell line, HIT T15", Febs Lett., vol. 239, pp. 185–189, 1988.

Knaus, H.G., et al., "Primary Sequence and Immunological Characterization of Beta–Subunit of High Conductance Ca2+–activated K+ Channel from Smooth Muscle", J. Biol. Chem., vol. 269, pp. 17274–17278, 1994.

Primary Examiner—David L. Fitzgerald
Attorney, Agent, or Firm—J. Antonio Garcia-Rivas; Valerie J. Camara; Mark R. Daniel

[57] ABSTRACT

This invention relates to a heteromultimer and its use in screening pharmaceutically active compounds for modulators of maxi-K channel activity. Such modulators are useful in treating asthma, pregnant human myometrium, hypertension and angina, cerebral ischemia and in conditions where stimulation of neurotransmitter release is desired such as Alzheimer's disease and stimulation of damaged nerves.

24 Claims, 4 Drawing Sheets

GCAGCCTCTT TTGGGTGGGG GCTGGGGACC AGGAAGAAAA
GGGTCTGCCGAAGACTCGCA GGGCACCCAG GAGACTAAAC
GTCTGCTGTC CCCAGTGGCCATGGGAAAGA AGCTGGTGAT
GGCCCAGAGG CGGGGAGAGA CTCGGGCCCTCTGCCTGGGG
GTGGCCATGG TCGTGGGCGC CGTCATCACC
TACTACATCTTAGGCACAAC TGTGCTGCCC CTCTATCAGA
AGAGTGTGTG GACCCAGGAATCCACGTGTC ACCTGATTGA
GACCAACATC AGGGACCAGG AGGAGCTGGAGGGCAAGAGG
GTGCCCAGT ACCCATGCCT GTGGGTCAAC
GTGTCGTCCGTGGGCCGCTG GGCTGTGCTG TACCACACGG
AGGACACGCG GGACCAGAACCACCAGTGCT CCTACATCCC
AAGCAGCCTG GACAACTACC AAGTGGCCCGGGCCGACGTG
GAGAAGGTCA GAGCCAGGTT CCACGAGAAC
CAGGATTTCTTCTGCTTCTC CACGACTCGG GAGAATGAGA
CCAGCGTCCT GTACCGGCGCCTCTATGGGC CCCAGAGCCT
CCTCTTCTCT CTCTTCTGGC CCACCTTTCTGCTGACTGGC
GGCCTGCTCA TCATTGTCAT GGTGAAGATC
AACCAGTCCCTGTCCATCCT GGCGGCCCAG AGGTAGATCC
ACACACTCCC ATCACCTCTCGGGCCGCTCT CGCTCGTGTC
CCGTGCCCCT CTCCTGCCTT CGCCCCTCCCCCTCCACTGC
ACGGATGGTC TTTGGGAAAT CCCTTAGTTA
AGTCATTTCCTGCTCAAGAC TGTTCAATGG CTCCTCAGGA
CCCAGGAGAA CTGAAGGTCAACCCGTGATG GTTCTCCATC
CTGGACCCCA CTCAGTCCAT CCATCTGAGTCAGTCCATCC
CTGACTCAAA TCTGTTTTCT GCTGTTCCAC
TGTCCACTGGACTGATGCCA ATGAGTCTCA CTTCTGTGCC
TGCTGGGCCC TCCCAGGAAGTGCTCCCCAA CAAGCCTCCA
TTCCTTCTTG GAATTCCAAA GTGAAAATAGCAGCAGCCCC
ATAGACACAG CACATTCATC AGTGGGACAT
CGCTTGTTTTCAGCTTTCTC AGCTCCGTAT ACTTCTTATA
CCGAATATTA ACAAATATAGTACAAACTTC TGGTCTTGAA

FIG. 1A

```
GTCATGGGGA TATAACTGCA ACATGGTGACAATAATTAGT
AATACTTTGC TGCATATTTG AAAGTTGCTG
AGAGAGTAGATCTTAAAAGC TCTCATCATA AGAAAAAAAA
CTGTCACTGT ATATGAGATGGGTGTTAACT AGAAACTGTT
GTGGTGATGA TTTTGTAATA CATACAGATATTGAATAATT
TTGTTACACA CTTGAAAACT AATATAATCT
TATATATTGATTATATCTCA AGAAACCAAA TATATACACA
ATATATAGGC TATAAGGAAATGATACTAAC ATACATAAAA
AACATTAACA GTGGGATTTA TTAATTGTAATTTTCTTCCT
TCCTTTNATT TTTTGTACTT TTCTAAATTT
TCAATAATAGAAAGGCTTGG TTTCACTGTG TTTATTTTA
ATCAGAACAG TAACAACAGATGTAATTTTG GAAAAATGTT
TGAAGGGGTA GGCTCCCCAT CATCAAGGCAGATGGAAGTC
GCCTAGTGGA CAGGTTGAAC TCCAATCAGA
CACAGGCTTTTTTTTTTAA TATTTATTTT TAATCGGCGG
ATAATCGCTT TACAGTGTTGCGTTGGTTTC TGCCATACAG
CACCATGAAT CGGCCACGGG TACACCTAAGACACGGACTT
GTGAGAACAC ACAAGTTTAA GAATCCTGGA
CAGAGGGAAAGTAAACACAG ATGGGGATTC ATGGTTTTCA
GTGTAGATTA AATACAAGGTACCTGGGCCT GCCCTGGCGG
TTCAGTGGTT CAGCAAGTGG TGAAGCAATGTCAAAGCAGG
AGACACAGTT CCTGATCCCT GGTATGTGAA
GGTTCCTTATGCGCTGAGCA ACCGAACCTG TTCACCACAA
CCACTGAGGC CGCCTTCTAGAGCCCACAAG CCAGAACCGC
TGAGCCCAGG TGCTGGAGCC GGTGCTCACACCCAGAGAAG
CCACTGCAAC GAGAAGCCCA CGCGCAGTGC
CGGGGAGTAGCCTCCACTCG TTACACCCAA AGACGTCCCC
ACACAGAGAC GAAGACCCAGGCGGCCGCTC TAGAACTAGT
GGATCCCCCG GGCTGCAGG
```

FIG. 1B

MGKKLVMAQR RGETRALCLG VAMVVGAVIT YYILGTTVLP
LYQKSVWTQESTCHLIETNI RDQEELEGKR VPQYPCLWVN
VSSVGRWAVL YHTEDTRDQNHQCSYIPSSL DNYQVARADV
EKVRARFHEN QDFFCFSTTR ENETSVLYRRLYGPQSLLFS
LFWPTFLLTG GLLIIVMVKI NQSLSILAAQ R

FIG. 2

MVKKLVMAQKRGETRALCLGVTMVVCAVITYYILVTTVLPL
YQKSVWTQESKCHLIETNIRDQEELKGKKVPQYPCLWVNVSA
AGRWAVLYHTEDTRDQNQQCSYIPGSVDNYQTARADVEKVR
AKFQEQQVFYCFSAPRGNETSVLFQRLYGPQALLFSLFWPTFL
LTGGLLIIAMVKSNQYLSILAAQK

FIG. 4

```
GAATTCCGGC TCTTTTGGGG TGGGGGCGGG GGTCCAGGCA
GAAAGAAACC GTCTGCTGCTCAAGACCCAC AGGACGCCGG
GAAGACTAAA TGATCACTGC CCCCAGTGAA TATGGTGAAG
AAGCTGGTGA TGGCCCAGAA GCGGGGAGAG ACACGAGCCC
TTTGCCTGGG TGTAACCATGGTGGTGTGTG CCGTCATCAC
CTACTACATC CTGGTCACGA CTGTGCTGCC CCTCTACCAG
AAAAGCGTGT GGACCCAGGA ATCCAAGTGC CACCTGATTG
AGACCAACAT CAGGGACCAGGAGGAGCTGA AGGGCAAGAA
GGTGCCCCAG TACCCATGCC TGTGGGTCAA CGTGTCAGCT
GCCGGCAGGT GGGCTGTGCT GTACCACACG GAGGACACTC
GGGACCAGAA CCAGCAGTGCTCCTACATCC CAGGCAGCGT
GGACAATTAC CAGACGGCCC GGGCCGACGT GGAGAAGGTC
AGAGCCAAAT TCCAAGAGCA GCAGGTCTTC TACTGCTTCT
CCGCACCTCG GGGGAACGAAACCAGCGTCC TATTCCAGCG
CCTCTACGGG CCCCAGGCCC TCCTCTTCTC CCTCTTCTGG
CCCACCTTCC TGCTGACCGG TGGCCTCCTC ATTATCGCCA
TGGTGAAGAG CAACCAGTACCTGTCCATCC TGGCGGCCCA
GAAGTAGAGC CATCCATCCA TGCCATACCA CTTGTCAGGG
CACAGGGGAC TGGCTGGGCC CCCAGGGCTG CTCCCCACTT
GCAGCACAAT GCCTTCTCCACCTGCCCTCC CACTCTTCCA
GTCCAATCCA CGCTGTCTTC TGTTGCAGGA CTAACCTTTG
AGAAATCCTT TTGTGAAGTC ATTGCCTGCT CGAAGAATGT
ACAGTGGCTC CCCAATGCCT TGGAGCCATA AGGCCAGCCA
GTTCTAGCTC TCTATTACCT GTCCCCACTC AACTGACTCA
TACCTGTTTC CGGCTGCATC ACTATGTGCC CCACAGAGAA
CGATGATCGT CACCTCTGTGCCTGAGTTCT CCCTGTTGTC
TCAAAGCGGT ACCCATCCTC CCCCAGAAGC TGTCCCCAGC
GAGCCTCCCT TCTTTGTTTG AATTCC
```

FIG. 3

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
   ( A ) LENGTH: 2238 base pairs
   ( B ) TYPE: nucleic acid
   ( C ) STRANDEDNESS: double
   ( D ) TOPOLOGY: linear ( i i ) MOLECULE TYPE: cDNA to mRNA ( x i ) SEQUENCE DESCRIPTION: SEQ ID NO:1:

```
GCAGCCTCTT TTGGGTGGGG GCTGGGGACC AGGAAGAAAA GGGTCTGCCG AAGACTCGCA      60
GGGCACCCAG GAGACTAAAC GTCTGCTGTC CCCAGTGGCC ATGGGAAAGA AGCTGGTGAT     120
GGCCCAGAGG CGGGGAGAGA CTCGGGCCCT CTGCCTGGGG GTGGCCATGG TCGTGGGCGC     180
CGTCATCACC TACTACATCT TAGGCACAAC TGTGCTGCCC CTCTATCAGA AGAGTGTGTG     240
GACCCAGGAA TCCACGTGTC ACCTGATTGA GACCAACATC AGGGACCAGG AGGAGCTGGA     300
GGGCAAGAGG GTGCCCCAGT ACCCATGCCT GTGGGTCAAC GTGTCGTCCG TGGGCCGCTG     360
GGCTGTGCTG TACCACACGG AGGACACGCG GGACCAGAAC CACCAGTGCT CCTACATCCC     420
AAGCAGCCTG GACAACTACC AAGTGGCCCG GGCCGACGTG GAGAAGGTCA GAGCCAGGTT     480
CCACGAGAAC CAGGATTTCT TCTGCTTCTC CACGACTCGG GAGAATGAGA CCAGCGTCCT     540
GTACCGGCGC CTCTATGGGC CCCAGAGCCT CCTCTTCTCT CTCTTCTGGC CCACCTTTCT     600
GCTGACTGGC GGCCTGCTCA TCATTGTCAT GGTGAAGATC AACCAGTCCC TGTCCATCCT     660
GGCGGCCCAG AGGTAGATCC ACACACTCCC ATCACCTCTC GGGCCGCTCT CGCTCGTGTC     720
CCGTGCCCCT CTCCTGCCTT CGCCCCTCCC CCTCCACTGC ACGGATGGTC TTTGGGAAAT     780
CCCTTAGTTA AGTCATTTCC TGCTCAAGAC TGTTCAATGG CTCCTCAGGA CCCAGGAGAA     840
CTGAAGGTCA ACCCGTGATG GTTCTCCATC CTGGACCCCA CTCAGTCCAT CCATCTGAGT     900
CAGTCCATCC CTGACTCAAA TCTGTTTTCT GCTGTTCCAC TGTCCACTGG ACTGATGCCA     960
ATGAGTCTCA CTTCTGTGCC TGCTGGGCCC TCCCAGGAAG TGCTCCCCAA CAAGCCTCCA    1020
TTCCTTCTTG GAATTCCAAA GTGAAAATAG CAGCAGCCCC ATAGACACAG CACATTCATC    1080
AGTGGGACAT CGCTTGTTTT CAGCTTTCTC AGCTCCGTAT ACTTCTTATA CCGAATATTA    1140
ACAAATATAG TACAAACTTC TGGTCTTGAA GTCATGGGA  TATAACTGCA ACATGGTGAC    1200
AATAATTAGT AATACTTTGC TGCATATTTG AAAGTTGCTG AGAGAGTAGA TCTTAAAAGC    1260
```

```
TCTCATCATA AGAAAAAAAA CTGTCACTGT ATATGAGATG GGTGTTAACT AGAAACTGTT     1320

GTGGTGATGA TTTTGTAATA CATACAGATA TTGAATAATT TTGTTACACA CTTGAAAACT     1380

AATATAATCT TATATATTGA TTATATCTCA AGAAACCAAA TATATACACA ATATATAGGC     1440

TATAAGGAAA TGATACTAAC ATACATAAAA AACATTAACA GTGGGATTTA TTAATTGTAA     1500

TTTTCTTCCT TCCTTTNATT TTTGTACTTT TCTAAATTTT CAATAATAGA AAGGCTTGGT     1560

TTCACTGTGT TTATTTTAA TCAGAACAGT AACAACAGAT GTAATTTTGG AAAAATGTTT      1620

GAAGGGGTAG GCTCCCCATC ATCAAGGCAG ATGGAAGTCG CCTAGTGGAC AGGTTGAACT     1680

CCAATCAGAC ACAGGCTTTT TTTTTTTAAT ATTTATTTTT AATCGGCGGA TAATCGCTTT    1740

ACAGTGTTGC GTTGGTTTCT GCCATACAGC ACCATGAATC GGCCACGGGT ACACCTAAGA     1800

CACGGACTTG TGAGAACACA CAAGTTTAAG AATCCTGGAC AGAGGGAAAG TAAACACAGA     1860

TGGGGATTCA TGGTTTTCAG TGTAGATTAA ATACAAGGTA CCTGGGCCTG CCCTGGCGGT     1920

TCAGTGGTTC AGCAAGTGGT GAAGCAATGT CAAAGCAGGA GACACAGTTC CTGATCCCTG     1980

GTATGTGAAG GTTCCTTATG CGCTGAGCAA CCGAACCTGT TCACCACAAC CACTGAGGCC     2040

GCCTTCTAGA GCCCACAAGC CAGAACCGCT GAGCCCAGGT GCTGGAGCCG GTGCTCACAC     2100

CCAGAGAAGC CACTGCAACG AGAAGCCCAC GCGCAGTGCC GGGGAGTAGC CTCCACTCGT     2160

TACACCCAAA GACGTCCCCA CACAGAGACG AAGACCCAGG CGGCCGCTCT AGAACTAGTG     2220

GATCCCCCGG GCTGCAGG                                                    2238
```

( 2 ) INFORMATION FOR SEQ ID NO:2:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:2:

```
Met Gly Lys Lys Leu Val Met Ala Gln Arg Arg Gly Glu Thr Arg Ala
  1               5                  10                  15

Leu Cys Leu Gly Val Ala Met Val Val Gly Ala Val Ile Thr Tyr Tyr
                 20                  25                  30

Ile Leu Gly Thr Thr Val Leu Pro Leu Tyr Gln Lys Ser Val Trp Thr
             35                  40                  45

Gln Glu Ser Thr Cys His Leu Ile Glu Thr Asn Ile Arg Asp Gln Glu
 50                  55                  60

Glu Leu Glu Gly Lys Arg Val Pro Gln Tyr Pro Cys Leu Trp Val Asn
 65                  70                  75                  80

Val Ser Ser Val Gly Arg Trp Ala Val Leu Tyr His Thr Glu Asp Thr
                 85                  90                  95

Arg Asp Gln Asn His Gln Cys Ser Tyr Ile Pro Ser Ser Leu Asp Asn
                100                 105                 110

Tyr Gln Val Ala Arg Ala Asp Val Glu Lys Val Arg Ala Arg Phe His
             115                 120                 125

Glu Asn Gln Asp Phe Phe Cys Phe Ser Thr Thr Arg Glu Asn Glu Thr
        130                 135                 140

Ser Val Leu Tyr Arg Arg Leu Tyr Gly Pro Gln Ser Leu Leu Phe Ser
145                 150                 155                 160

Leu Phe Trp Pro Thr Phe Leu Leu Thr Gly Gly Leu Leu Ile Ile Val
                165                 170                 175
```

|     | Met | Val | Lys | Ile | Asn | Gln | Ser | Leu | Ser | Ile | Leu | Ala | Ala | Gln | Arg |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

( 2 ) INFORMATION FOR SEQ ID NO:3:

( i ) SEQUENCE CHARACTERISTICS:
        ( A ) LENGTH: 1106 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:3:

```
GAATTCCGGC TCTTTTGGGG TGGGGCGGG  GGTCCAGGCA GAAAGAAACC GTCTGCTGCT      60
CAAGACCCAC AGGACGCCGG GAAGACTAAA TGATCACTGC CCCCAGTGAA TATGGTGAAG     120
AAGCTGGTGA TGGCCCAGAA GCGGGGAGAG ACACGAGCCC TTTGCCTGGG TGTAACCATG     180
GTGGTGTGTG CCGTCATCAC CTACTACATC CTGGTCACGA CTGTGCTGCC CCTCTACCAG     240
AAAAGCGTGT GGACCCAGGA ATCCAAGTGC CACCTGATTG AGACCAACAT CAGGGACCAG     300
GAGGAGCTGA AGGGCAAGAA GGTGCCCCAG TACCCATGCC TGTGGGTCAA CGTGTCAGCT     360
GCCGGCAGGT GGGCTGTGCT GTACCACACG GAGGACACTC GGGACCAGAA CCAGCAGTGC     420
TCCTACATCC CAGGCAGCGT GGACAATTAC CAGACGGCCC GGGCCGACGT GGAGAAGGTC     480
AGAGCCAAAT TCCAAGAGCA GCAGGTCTTC TACTGCTTCT CCGCACCTCG GGGAACGAA      540
ACCAGCGTCC TATTCCAGCG CCTCTACGGG CCCCAGGCCC TCCTCTTCTC CCTCTTCTGG     600
CCCACCTTCC TGCTGACCGG TGGCCTCCTC ATTATCGCCA TGGTGAAGAG CAACCAGTAC     660
CTGTCCATCC TGGCGGCCCA GAAGTAGAGC CATCCATCCA TGCCATACCA CTTGTCAGGG     720
CACAGGGGAC TGGCTGGGCC CCCAGGGCTG CTCCCCACTT GCAGCACAAT GCCTTCTCCA     780
CCTGCCCTCC CACTCTTCCA GTCCAATCCA CGCTGTCTTC TGTTGCAGGA CTAACCTTTG     840
AGAAATCCTT TTGTGAAGTC ATTGCCTGCT CGAAGAATGT ACAGTGGCTC CCCAATGCCT     900
TGGAGCCATA AGGCCAGCCA GTTCTAGCTC TCTATTACCT GTCCCCACTC AACTGACTCA     960
TACCTGTTTC CGGCTGCATC ACTATGTGCC CCACAGAGAA CGATGATCGT CACCTCTGTG    1020
CCTGAGTTCT CCCTGTTGTC TCAAAGCGGT ACCCATCCTC CCCCAGAAGC TGTCCCCAGC    1080
GAGCCTCCCT TCTTTGTTTG AATTCC                                       1106
```

( 2 ) INFORMATION FOR SEQ ID NO:4:

( i ) SEQUENCE CHARACTERISTICS:
        ( A ) LENGTH: 191 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:4:

| Met | Val | Lys | Lys | Leu | Val | Met | Ala | Gln | Lys | Arg | Gly | Glu | Thr | Arg | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Cys | Leu | Gly | Val | Thr | Met | Val | Val | Cys | Ala | Val | Ile | Thr | Tyr | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ile | Leu | Val | Thr | Thr | Val | Leu | Pro | Leu | Tyr | Gln | Lys | Ser | Val | Trp | Thr |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Gln | Glu | Ser | Lys | Cys | His | Leu | Ile | Glu | Thr | Asn | Ile | Arg | Asp | Gln | Glu |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Glu | Leu | Lys | Gly | Lys | Lys | Val | Pro | Gln | Tyr | Pro | Cys | Leu | Trp | Val | Asn |
|-----|-----|-----|-----|-----|-----|-----|-----|-----|-----|-----|-----|-----|-----|-----|-----|

-continued

| 65 | | | | | 70 | | | | 75 | | | | | 80 |
|---|---|---|---|---|---|---|---|---|---|---|---|---|---|---|
| Val | Ser | Ala | Ala | Gly 85 | Arg | Trp | Ala | Val | Leu 90 | Tyr | His | Thr | Glu | Asp 95 | Thr |
| Arg | Asp | Gln | Asn 100 | Gln | Gln | Cys | Ser | Tyr 105 | Ile | Pro | Gly | Ser | Val 110 | Asp | Asn |
| Tyr | Gln | Thr 115 | Ala | Arg | Ala | Asp | Val 120 | Glu | Lys | Val | Arg | Ala 125 | Lys | Phe | Gln |
| Glu | Gln 130 | Gln | Val | Phe | Tyr | Cys 135 | Phe | Ser | Ala | Pro | Arg 140 | Gly | Asn | Glu | Thr |
| Ser 145 | Val | Leu | Phe | Gln | Arg 150 | Leu | Tyr | Gly | Pro | Gln 155 | Ala | Leu | Leu | Phe | Ser 160 |
| Leu | Phe | Trp | Pro | Thr 165 | Phe | Leu | Leu | Thr | Gly 170 | Gly | Leu | Leu | Ile | Ile 175 | Ala |
| Met | Val | Lys | Ser 180 | Asn | Gln | Tyr | Leu | Ser 185 | Ile | Leu | Ala | Ala | Gln 190 | Lys | |

DNA ENCODING THE β SUBUNIT OF A MAMMALIAN MAXI-K POTASSIUM CHANNEL

This application is a continuation-in-part of application Ser. No. 08/389,668 filed 16 Feb. 1995, now U.S. Pat. No. 5,637,470, which is in turn a continuation-in-part of application Ser. No. 08/242,811, filed 13 May 1994, now abandoned.

BACKGROUND OF THE INVENTION

This invention relates to a novel heteromultimer and its use in screening pharmaceutically active compounds for modulators of maxi-K channel activity. Such modulators are useful in treating asthma, pregnant human myometrium, cerebral ischemia and in conditions where stimulation of neurotransmitter release is desired such as Alzheimer's disease and stimulation of damaged nerves.

The present invention relates to the combined use of both the α and β subunit of a mammalian calcium-activated potassium channel originally identified and separated from bovine tracheal smooth muscle, which confers pharmacological properties to the α and β subunit complex similar to that found with the native channel. It further relates to the use of the α-β heteromultimer in expression systems as assays for agonists or antagonists of calcium-activated potassium channels.

Potassium channel antagonists are useful for a number of physiological disorders in mammals, including humans. Ion channels, including potassium channels, are found in all mammalian cells and are involved in the modulation of various physiological processes and normal cellular homeostasis. Potassium channels generally control the resting membrane potential, and the efflux of potassium ions causes repolarization of the plasma membrane after cell depolarization. Potassium channel antagonists prevent repolarization and cause the cell to stay in the depolarized, excited state.

There are a number of potassium channel subtypes. Physiologically, one important subtype is the maxi-K channel, defined as high-conductance calcium-activated potassium channel, which is present in neuronal tissue and smooth muscle. Intracellular calcium concentration ($Ca^{2+}i$) and membrane potential gate these channels. For example, maxi-K channels are opened to enable efflux of potassium ions by an increase in the intracellular $Ca^{2+}$ concentration or by membrane depolarization (change in potential). Elevation of intracellular calcium concentration is required for neurotransmitter release, smooth muscle contraction, proliferation of some cell types and other processes. Modulation of maxi-K channel activity therefore affects cellular processes that depend on influx of calcium through voltage-dependent pathways, such as transmitter release from the nerve terminals and smooth muscle contraction. The screening procedures revealed by the present invention are therefore useful for detecting compounds with utility in the treatment of neurological disorders in which neurotransmitter release is impaired.

A number of marketed drugs function as potassium channel antagonists. The most important of these include the compounds Glyburide, Glipizide and Tolbutamide. These potassium channel antagonists are useful as antidiabetic agents. Potassium channel antagonists are also utilized as Class III antiarrhythmic agents and to treat acute infractions in humans. A number of naturally occurring toxins are known to block potassium channels including apamin, iberiotoxin, charybdotoxin, margatoxin, noxiustoxin, kaliotoxin, dendrotoxin(s), mast cell degranuating (MCD) peptide, and β-bungarotoxin (β-BTX).

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

It is believed that certain diseases such as depression, memory disorders and Alzheimer's disease are the result of an impairment in neurotransmitter release. Potassium channel antagonists may therefore be utilized as cell excitants which should stimulate release of neurotransmitters such as acetylcholine, serotonin and dopamine. Enhanced neurotransmitter release should reverse the symptoms associated with depression and Alzheimer's disease.

The present invention relates to the use of the calcium activated potassium channel α and β subunits in transient or stable coexpression systems as assays for antagonists of maxi-K channels. Such blockers are useful in diseases where neurotransmission is deficient, such as Alzheimer's or depression.

The present invention also relates to the use of the α and β subunits in transient or stable coexpression systems as assays to screen for agonists of maxi-K channels. Such agonists are useful in diseases involving excessive smooth muscle tone or excitability such as asthma, angina, hypertension, incontinence, pre-term labor, migraine, cerebral ischemia and irritable bowl syndrome. Such agonists also act to decrease neurotransmitter or hormone release, and thus are of use in treating diseases such as asthma, cerebral ischemia and pain modulation. Specifically such agents can act to decrease release of tachykinins, such as substance P and neurokinin A, among others, that are involved in the neurogenic inflammation that occurs in asthma. Thus, agonists of maxi-K channels would be expected to decrease neurogenic inflammation and be useful in the treatment of asthma.

Agonists of maxi-K channels hyperpolarize neurons and thereby, decrease calcium entry through both voltage-dependent calcium channels and through excitatory neurotransmitter activated channels. Since elevation of intracellular calcium is part of the process which leads to cell damage, reduction in calcium entry would decrease neural damage in cerebral ischemia.

SUMMARY OF THE INVENTION

The present invention is directed to an isolated and purified DNA molecule which encodes a β subunit of a mammalian calcium activated potassium channel or a functional derivative thereof. It is further directed to an expression vector for expression of a β subunit of a mammalian calcium-activated potassium channel in a recombinant host, wherein said vector contains a recombinant gene encoding a β subunit of a mammalian calcium-activated potassium channel or functional derivative thereof. Further this novel invention is directed to a recombinant host cell containing a recombinantly cloned gene encoding a β subunit of a mammalian calcium-activated potassium channel or functional derivative thereof. In addition, the instant invention is directed to a protein, in substantially pure form which functions as a β subunit of a mammalian calcium-activated potassium channel. The invention is also directed to a monospecific antibody immunologically reactive with a β subunit of a mammalian calcium-activated potassium channel and a process for expression of a β subunit of a mammalian calcium-activated potassium channel protein in a recombinant host cell, comprising:

(a) transferring the expression vector containing a recombinant gene encoding αβ subunit of a mammalian calcium-activated potassium channel or functional derivative thereof into suitable host cells; and (b) culturing the host cells of step (a) under conditions which allow expression of the β subunit of a mammalian high-conductance, calcium-activated potassium channel protein from the expression vector.

Further, this invention is directed to a novel method of identifying compounds that modulate β subunit of a mammalian calcium-activated potassium channel activity, comprising:

(a) combining a suspected modulator of β subunit of a mammalian high-conductance, calcium-activated potassium channel activity with α and β subunits of a mammalian high-conductance, calcium-activated potassium channel; and (b) measuring an effect of the modulator on the channel.

In addition, this invention is directed to a novel method of identifying compounds that modulate the activity of a heteromultimer of α and β subunits of a mammalian calcium-activated potassium channel, comprising:

(a) combining a suspected modulator of a mammalian calcium-activated potassium channel activity with α and β subunits of a calcium-activated potassium channel; and (b) measuring an effect of the modulator on the heteromultimer.

This invention is also directed to a compound active in the aforementioned method, wherein said compound is a modulator of a mammalian calcium-activated potassium channel. Further, this invention is directed to a pharmaceutical composition comprising a compound active in the aforementioned method, wherein said compound is a modulator of mammalian calcium-activated potassium channel activity. Additionally, this invention is directed to a novel treatment of a patient in need of such treatment for a condition which is mediated by a mammalian calcium-activated potassium channel, comprising administration of an α and β subunit of a mammalian calcium-activated potassium channel modulating compound active in the aforementioned method. This invention is further directed to a method of treating a patient in need of such treatment for a condition which is mediated by a mammalian calcium-activated potassium channel and is characterized by alterations in smooth muscle tone, release of neurotransmitter substances or hormones and excitability of neurons, comprising administration of an α and β subunit of a mammalian calcium-activated potassium channel modulating compound active in the above mentioned method. This invention is also directed to a method of identifying compounds that modulate mammalian calcium-activated potassium channel activity, comprising:

(a) combining a suspected modulator of β subunit of a mammalian calcium-activated potassium channel activity with a cell expressing recombinant α and β subunit of a mammalian calcium-activated potassium channel; and (b) measuring an effect of the modulator on the channel.

This invention is also directed to a compound active in the method of identifying compounds that modulate mammalian calcium-activated potassium channel activity wherein said compound is a modulator of a heteromultimer composed of the α and β subunit of a mammalian calcium-activated potassium channel. This invention is also directed to a method of treating a patient in need of such treatment for a condition which is mediated by a β subunit, comprising administration of a β subunit of a mammalian calcium-activated potassium channel modulating compound active in the method of identifying compounds that modulate mammalian calcium-activated potassium channel activity. This invention is also directed to a method of treating a patient in need of such treatment for a condition which is mediated by a β subunit of a mammalian calcium-activated potassium channel and is characterized by inflammation, hypercontractility of smooth muscle, neural ischemia, or neural degeneration, comprising administration of a β subunit of a mammalian calcium-activated potassium channel modulating compound active in the method of identifying compounds that modulate mammalian calcium-activated potassium channel activity.

BRIEF DESCRIPTION OF THE FIGURES

FIGS. 1A–B contain Sequence No. 1 which is the isolated and purified DNA molecule which encodes a β-subunit of a mammalian (bovine) high-conductance, calcium activated potassium channel.

FIG. 2 contains Sequence No. 2 which is the amino acid sequence of β subunit (bovine). The amino acids shown in Sequence No. 2 are represented by a single letter. The legend for these amino acids is as follows:

| Amino Acid | One Letter |
| --- | --- |
| Alanine | A |
| Arginine | R |
| Asparagine | N |
| Aspartic | D |
| Asparagine or Aspartic | B |
| Cysteine | C |
| Glycine | G |
| Glutamine | Q |
| Glutamic | E |
| Glutamine or Glutamic | Z |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

FIG. 3 contains Sequence No. 3 which is the isolated and purified DNA molecule which encodes a β-subunit of a human high-conductance, calcium activated potassium channel.

FIG. 4 contains Sequence No. 4 which is the amino acid sequence of human β-subunit. The amino acids shown in Sequence No. 4 are represented by a single letter. The legend for these amino acids is as shown above for FIG. 4.

DETAILED DESCRIPTION OF THE INVENTION

The present invention relates to DNA encoding a beta-subunit of a mammalian calcium-activated potassium channel (β subunit) which was isolated from β subunit producing cells.

By "calcium activated potassium channel" is meant high conductance, intermediate conductance or small conductance calcium activated potassium channels. In general, the "high conductance channel", also known as the "maxi-K channel", is defined as having greater than 200 pS conductance in a membrance exposed to about 150 mμ KCl on both sides.

The isolated and purified DNA molecule which encodes a β subunit of a bovine high-conductance, calcium activated potassium channel has a nucleotide sequence shown in FIGS. 1A–B as Sequence No. 1.

"β subunit", as used herein, refers to protein which can specifically function as the β subunit of mammalian calcium-activated potassium channels. The amino acid sequence of bovine β subunit is shown in FIG. 2, as Sequence No. 2.

The isolated and purified DNA molecule which encodes a β subunit of a human high-conductance, calcium activated potassium channel has a nucleotide sequence shown in FIG. 3 as Sequence No. 3.

The amino acid sequence of human β subunit is shown in FIG. 4, as Sequence No. 4.

High-conductance calcium-activated potassium (maxi-K) channels in smooth muscle are composed of two distinct subunits, α and β (M. Garcia-Calvo, H. -G. Knaus, O. B. McManus, K. M. Giangiacomo, G. J. Kaczorowski and M. L. Garcia, *The Journal of Biological Chemistry* 269, 676–683 (1994)). Peptide sequence derived from the α subunit is homologous to the protein product of the mSlo gene and is therefore a member of the mSlo gene family (H. -G. Knaus, M. Garcia-Calvo, G. J. Kaczorowski and M. L. Garcia, *The Journal of Biological Chemistry* 269, 3921–3924 (1994)). mSlo is a mouse homologue (A. Butler, S. Tsunoda, D. P. McCobb, A. Wei and L. Salkoff, *Science* 261, 221–224 (1993)) of the gene product from the Drosophila gene locus that is disrupted in slowpoke mutants that lack calcium-activated potassium channels (N. S. Atkinson, G. A. Robertson and B. Ganetzky, *Science* 253, 551–555 (1991)). RNA transcribed in vitro from mSlo cDNA and injected into Xenopus oocytes caused the expression of calcium-activated potassium channels with a large single channel conductance indicating that the mSlo gene product is a structural component of maxi-K channels.

The amino acid and DNA sequences of the β subunit were not previously known. Discovery of the β subunit required purification and functional reconstitution of the maxi-K channel from bovine smooth muscle (M. Garcia-Calvo, H. -G. Knaus, O. B. McManus, K. M. Giangiacomo, G. J. Kaczorowski and M. L. Garcia, *The Journal of Biological Chemistry* 269, 676–683 (1994)). The channel purified from bovine tracheal smooth muscle possessed the properties of the native channel from that tissue. $^{125}$I-ChTX bound to the purified channel with a binding affinity similar to the affinity for $^{125}$I-ChTX binding to the native maxi-K channel. Binding of $^{125}$I-ChTX to the purified maxi-K channel was inhibited by ChTX, iberiotoxin (IbTX), limbatustoxin (LbTX), barium, potassium, cesium and tetraethylammonium in a manner similar to inhibition by these compounds of $^{125}$I-ChTX binding to maxi-K channels found in native tissue. Thus, the pharmacological properties of the purified channels resembled the maxi-K channels found in native tissues. Direct evidence that the purified channel is the maxi-K channel found in native tissue comes from reconstitution experiments. Proteoliposomes containing the purified channel were fused with planar lipid bilayers. Channels were then observed with a large single channel conductance (>200 pS) that were selectively permeable to potassium, and whose open probability was increased by increasing concentrations of intracellular calcium and by membrane depolarization. These are the biophysical properties of maxi-K channels observed in native tissues.

The purified β subunit is a glycoprotein with an Mr of 31 kDa. Deglycosylation studies suggest that carbohydrate is attached to the β subunit by N-linked glycosylation at least at two sites, and that the β subunit is the protein to which $^{125}$I-ChTX becomes covalently linked to the maxi-K channel with the bifunctional crosslinking reagent, disuccinimidyl suberate (M. Garcia-Calvo, H. -G. Knaus, O. B. McManus, K. M. Giangiacomo, G. J. Kaczorowski and M. L. Garcia, *The Journal of Biological Chemistry* 269, 676–683 (1994)). Peptide sequencing of a proteolytic fragment obtained from the purified β subunit revealed a unique sequence that was used to construct oligonucleotide probes with which cDNAs encoding the β subunit were isolated. The cDNAs encode a protein with little sequence homology to subunits of other known ion channels. The cDNAs encode a protein containing 191 amino acids with two hydrophobic regions that may form transmembrane domains and two potential sites for N-linked glycosylation at asparagine residues located in the putative extracellular domain. Antibodies raised against peptide sequences contained in the putative extracellular domain of the β subunit specifically immunoprecipitated β subunit labeled with $^{125}$I Bolton-Hunter reagent, as well as the $^{125}$I-ChTX crosslinked β subunit. Under non-denaturing conditions, anti-β subunit anti-sera specifically immunoprecipitated a complex containing both the α and β subunits. Therefore, the purified and cloned β subunit described herein is part of the complex comprising the maxi-K channel.

Direct evidence that the β subunit described herein is a functional part of the maxi-K channel comes from coexpression studies with α and β subunits. The cDNA encoding the β subunit was used to synthesize cRNA in vitro. This cRNA was injected into Xenopus oocytes along with cRNA encoding an α subunit isolated from mouse brain (GenBank Accession #U09383). Membrane currents in the oocytes were measured with standard two microelectrode voltage-clamp methods. Membrane patches were excised from oocytes in the inside-out configuration, and currents through these patches were measured with patch-clamp methods. In these excised-patch experiments, both the membrane potential and intracellular calcium concentration were controlled. Oocytes injected with cRNA encoding the β subunit alone did not exhibit any currents that were distinguishable from background currents observed in uninjected oocytes. Oocytes injected with cRNA encoding the α subunit alone exhibited outward potassium currents that were blocked by ChTX and IbTX. Membrane patches excised from oocytes injected with cRNA encoding α alone contained large-conductance (>200 pS) potassium channels that were selective for potassium over sodium, and whose open probability was increased by increasing intracellular calcium and by membrane depolarization. The open probability of channels from oocytes injected with cRNA encoding the α subunit alone was not increased after exposure to 100–500 nM of dehydrosoyasaponin I (DHS-I), a potent activator of maxi-K channels from aortic and tracheal smooth muscle (O. B. McManus, G. H. Harris, K. M. Giagiacomo, P. Feigenbaum, J. P. Reuben, M. E. Addy, J. F. Burka, G. J. Kaczorowski and M. L. Garcia, *Biochemistry* 32, 6128–6133 (1993)).

Oocytes injected with cRNAs encoding both the α and β subunits exhibited outward potassium currents that were blocked by ChTX and IbTX. These currents were expressed at amplitudes similar to the currents observed in oocytes injected with cRNAs encoding the α subunit alone. The outward currents observed in oocytes injected with α and β subunits were activated at more negative potentials than the oocytes injected with α subunit cRNA alone. Direct evidence for a difference in channel gating between channels in oocytes injected with cRNA encoding the α subunit alone, and channels in oocytes injected with cRNAs encoding both the α and β subunits, comes from recordings of currents in membrane patches excised from each type of oocyte. Maxi-K channels observed in α and β subunit-injected oocytes had a large single channel conductance (>200 pS), and these channels were selective for potassium over sodium. The open probability of these channels was increased by increasing intracellular calcium concentrations and by membrane depolarization. The gating of the channels in oocytes injected with both α and β subunit cRNAs differed from the gating of channels from oocytes injected with α subunit cRNA alone. The channels from oocytes expressing both subunits were activated at more negative membrane potentials than were channels expressing the α sub-unit alone. At a given concentration of intracellular calcium, channels from oocytes expressing both subunits were activated at membrane potentials 50 to 100 mV more negative than were channels from oocytes expressing the α subunit alone. Channels from oocytes expressing both subunits were fully activated by 100–300 nM of DHS-I applied to the intracellular face of the channel. Thus, addition of the β subunit shifted the voltage-dependence of gating of channels encoded by the α subunit and conferred sensitivity to an activator of maxi-K channels. Therefore, the β subunit co-assembles with the α subunit and forms calcium-activated potassium channels with pharmacological and biophysical properties that differ from calcium-activated potassium channels encoded by the α subunit alone and which more closely resemble maxi-K channels in native tissues.

The α and β subunits can be transiently or stably co-expressed in cell lines that can then be used to screen for modulators of calcium-activated potassium channels. Cell lines expressing both subunits offer advantages over cell lines expressing the α subunit alone. Coexpression of the α and β subunits produces novel hetero-multimeric channels whose gating is more sensitive to intracellular calcium and depolarizing membrane potential. Such hetero-multimeric channels can be more easily induced to open and thus provide a more sensitive assay system for agents that open maxi-K channels and for agents that block maxi-K channels.

DNA encoding the β subunit from bovine trachea may be used to isolate and purify homologues of β subunits from other organisms, including humans. To accomplish this, the first β subunit DNA may be mixed with a sample containing DNA encoding homologues of β subunit under appropriate hybridization conditions. The hybridized DNA complex may be isolated and the DNA encoding the homologous DNA may be purified therefrom.

Because the genetic code is degenerate, more than one codon may be used to encode a particular amino acid, and therefore, the amino acid sequence can be encoded by any of a set of similar DNA oligonucleotides. Only one member of the set will be identical to the β subunit sequence, but will be capable of hybridizing to β subunit DNA even in the presence of DNA oligonucleotides with mismatches under appropriate conditions. Under alternate conditions, the mismatched DNA oligonucleotides may still hybridize to the β subunit DNA to permit identification and isolation of β subunit encoding DNA.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include, but are not limited to changes in the affinity of an enzyme for a substrate or a receptor for a ligand.

As used herein, a "functional derivative" of β subunit is a compound that possesses a biological activity (either functional or structural) that is substantially similar to the biological activity of β subunit. The term "functional derivatives" is intended to include the "fragments," "variants," "degenerate variants," "analogs" and "homologues", and to "chemical derivatives" of β subunit. The term "fragment" is meant to refer to any polypeptide subset of β subunit. The term "variant" is meant to refer to a molecule substantially similar in structure and function to either the entire β subunit molecule or to a fragment thereof. A molecule is "substantially similar" to β subunit if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire β subunit molecule, or to a fragment thereof.

The cloned β subunit DNA obtained through the methods described herein may be recombinantly expressed by molecular cloning into an expression vector containing a suitable promoter and other appropriate transcription regulatory elements, and transferred into prokaryotic or eukaryotic host cells to produce recombinant β subunit. Techniques for such manipulations are fully described in Sambrook, J., et al., Molecular Cloning Second Edition, 1990, Cold Spring Harbor Press and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast, or bacteria-animal cells, or bacteria-fungal cells, or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant β subunit in mammalian cells along with the α subunit. Commercially available mammalian expression vectors which are suitable for recombinant β subunit expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

A variety of bacterial expression vectors may be used to express recombinant β subunit in bacterial cells along with the α subunit. Commercially available bacterial expression vectors which may be suitable for recombinant β subunit expression include, but are not limited to pET11a (Novagen), lambda gt11 (Invitrogen), pcDNAII (Invitrogen), pKK223-3 (Pharmacia).

A variety of insect cell expression vectors may be used to express recombinant β subunit in insect cells along with the α subunit. Commercially available insect cell expression vectors which may be suitable for recombinant expression of β subunit include but are not limited to pBlue Bac III (Invitrogen).

An expression vector containing DNA encoding β subunit may be used for expression of β subunit in a recombinant host cell along with the α subunit. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells expressing the α subunit via any one of a number of techniques including but not limited to transformation, transfection, lipofection, protoplast fusion, and electroporation. The expression vector-containing cells are clonally propagated and individually analyzed to determine whether they produce β subunit protein. Identification of β subunit expressing host cell clones also expressing the α subunit may be done by several means, including but not limited to immunological reactivity with anti-β subunit antibodies, and the presence of host cell-associated β subunit activity, such as sensitivity of expressed maxi-K channels to DHS-I, and ability to covalently cross-link $^{125}$I-ChTX to the β subunit with the bifunctional cross-linking reagent disuccinimidyl suberate or similar cross-linking reagents.

Co-expression of α and β subunit DNAs may also be performed using in vitro produced synthetic mRNA or native mRNA. Synthetic mRNA or mRNA isolated from α and β subunit producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of β subunit in a recombinant host cell which may also be expressing the α subunit, β subunit protein or maxi-K channels consisting of α-β heteromultimers may be recovered to provide β subunit or maxi-K channels in purified form. Several β subunit and maxi-K channel purification procedures are available and suitable for use. As described herein, recombinant β subunit and maxi-K channels may be purified from cell lysates and extracts by various combinations of, or individual application of salt fractionation, ion exchange chromatography, size exclusion chromatography, hydroxylapatite adsorption chromatography and hydrophobic interaction chromatography.

In addition, recombinant β subunit and maxi-K channels can be separated from other cellular proteins by use of an immunoaffinity column made with monoclonal or polyclonal antibodies specific for full length nascent β subunit, or polypeptide fragments of β subunit.

Monospecific antibodies to β subunit are purified from mammalian antisera containing antibodies reactive against β subunit or are prepared as monoclonal antibodies reactive with β subunit using the technique of Kohler and Milstein, Nature 256, 495–497 (1975). Mono-specific antibody as used herein is defined as a single antibody species or multiple antibody species with homogenous binding characteristics for β subunit. Homogenous binding as used herein refers to the ability of the antibody species to bind to a specific antigen or epitope, such as those associated with the β subunit, as described above. β subunit specific antibodies are raised by immunizing animals such as mice, rats, guinea pigs, rabbits, goats, horses and the like, with rabbits being preferred, with an appropriate concentration of β subunit either with or without an immune adjuvant.

Preimmune serum is collected prior to the first immunization. Each animal receives between about 0.1 mg and about 1000 mg of β subunit associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consists of β subunit in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with β subunit are prepared by immunizing inbred mice, preferably Balb/c, with β subunit. The mice are immunized by the IP or SC route with about 0.1 mg to about 10 mg, preferably about 1 mg, of β subunit in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of β subunit in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using β subunit as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in *Tissue Culture Methods and Applications*, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-β subunit mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of β subunit in body fluids or tissue and cell extracts.

It is readily apparent to those skilled in the art that the above described methods for producing monospecific antibodies may be utilized to produce antibodies specific for β subunit polypeptide fragments, or the full-length nascent β subunit polypeptide. Specifically, it is readily apparent to those skilled in the art that monospecific antibodies may be generated which are specific for the fully functional receptor or fragments thereof.

β subunit antibody affinity columns are made by adding the antibodies to Affigel-10 (Biorad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts containing β subunit or maxi-K channels made using appropriate membrane solubilizing detergents are slowly passed through the column. The column is then washed with phosphate buffered saline/detergent until the optical density ($A_{280}$) falls to background, then the protein is eluted with 0.23M glycine-HCl (pH 2.6)/detergent. The purified β subunit protein or maxi-K channel is then dialyzed against phosphate buffered saline/detergent.

The present invention is also directed to methods for screening for compounds which modulate the expression of DNA or RNA encoding β subunit, as well as the function of β subunit protein in vivo. Compounds which modulate these activities may be DNA, RNA, peptides, proteins, or non-proteinaceous organic molecules. Compounds may modulate by increasing or attenuating the expression of DNA or RNA encoding β subunit, or the function of β subunit protein. Compounds that modulate the expression of DNA or RNA encoding β subunit or the function of β subunit protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing β subunit DNA, antibodies to β subunit, or β subunit protein may be prepared. Such kits are used to detect DNA which hybridizes to β subunit DNA, or to detect the presence of β subunit protein or peptide fragments in a sample. Such characterization is useful for a variety of purposes including, but not limited to, forensic analyses and epidemiological studies.

The DNA molecules, RNA molecules, recombinant protein and antibodies of the present invention may be used to screen and measure levels of β subunit DNA, β subunit RNA or β subunit protein. The recombinant proteins, DNA molecules, RNA molecules and antibodies lend themselves to the formulation of kits suitable for the detection and typing of β subunit. Such a kit would comprise a compartmentalized carrier suitable to hold in close confinement at least one container. The carrier would further comprise reagents such as recombinant β subunit protein or anti-β subunit antibodies suitable for detecting β subunit. The carrier may also contain a means for detection such as labeled antigen or enzyme substrates or the like.

Nucleotide sequences that are complementary to the β sub-unit encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other β subunit antisense oligonucleotide mimetics. β subunit antisense molecules may be introduced into cells by microinjection, liposome encapsulation or by expression from vectors harboring the antisense sequence. β subunit antisense therapy may be particularly useful for the treatment of diseases where it is beneficial to reduce β subunit or maxi-K channel activity.

β subunit gene therapy may be used to introduce β subunit into the cells of target organs. The β subunit gene can be ligated into viral vectors which mediate transfer of the β subunit DNA by infection of recipient host cells. Suitable viral vectors include retrovirus, adenovirus, adeno-associated virus, herpes virus, vaccinia virus, polio virus and the like. Alternatively, β subunit DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo β subunit gene therapy. β subunit gene therapy may be particularly useful for the treatment of diseases where it is beneficial to elevate β subunit activity.

Pharmaceutically useful compositions comprising β subunit DNA, β subunit RNA, or β subunit protein, or modulators of β subunit or maxi-K channel activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose β subunit or maxi-K channel related disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal modulation of a maxi-K channel that consists of α and β subunits, or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient for use in the modulation of maxi-K channels can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form all using forms well known to those of ordinary skill in the pharmaceutical arts. An effective but non-toxic amount of the compound desired can be employed as a β subunit or maxi-K channel modulating agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of the β subunit or maxi-K channel modulators are adjusted when combined to achieve desired effects. On the other hand, dosages of these various agents may be independently optimized and combined to achieve a synergistic result wherein the pathology is reduced more than it would be if either agent were used alone.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. Dosage forms that provide for sustained or continuous delivery of these compounds is also within the scope of this invention.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers, which are collectively referred to herein as "carrier" materials, suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthum gum and the like.

For liquid forms the active drug component can be combined in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following examples illustrate the present invention without, however, limiting the same thereto.

EXAMPLE 1

Purification of the β Subunit of High-Conductance Calcium-Activated Potassium Channels Purified sarcolemmal membrane vesicles derived from bovine tracheal smooth muscle were prepared as previously described (Slaughter, R. S., Shevell, J. L., Felix, J. P., Garcia, M. L., and Kaczorowski, G. J., *Biochemistry* 28, 3995–4002 (1989)). The interaction of [$^{125}$I]ChTX (New England Nuclear Corporation) with maxi-K channels in bovine tracheal sarcolemmal membrane vesicles was monitored as outlined previously (Vazquez, J., Feigenbaum, P., Katz, G., King, V. F., Reuben, J. P., Roy-Contancin, L., Slaughter, R. S., Kaczorowski, G. J., and Garcia, M. L., *J. Biol. Chem.* 264, 20902–20909 (1989)). Binding of radiolabeled toxin to solubilized channels was measured by incubating aliquots of solubilized material in 0.05% digitonin with [$^{125}$I]ChTX as described (Garcia-Calvo, M., Vazquez, J., Smith, M., Kaczorowski, G. J., and Garcia, M. L. *Biochemistry* 30, 11157–11164 (1991)). At the end of the incubation period, protein was precipitated by addition of 10% (w/v) PEG (Mw~8000) in the presence of δ-globulin and the precipitate was immediately collected onto GF/C glass fiber filters (Whatman) that had been presoaked in 0.5% polyethylenimine. Nonspecific binding was determined in the presence of 10 nM ChTX (Peninsula Laboratories). For each experiment, triplicate assays were routinely performed, and the data were averaged. The standard error of the mean of these replicates was typically less than 3%.

All buffers employed for solubilization and during purification contained 1 mM iodoacetamide, 0.1 mM PMSF, 0.1 mM benzamidine. Protein concentration was determined using either the Bradford (Bradford, M. M. (1976) *Anal. Biochem.* 72, 248–254) or the Gold (Stoschek, C. M. (1987) *Anal. Biochem.* 160, 301–305) method with bovine serum albumin as standard. Membranes derived from 250 cow tracheas (ca. 10 gr of purified sarcolemmal membrane vesicle protein) were solubilized with 0.5% digitonin for 10 min at 4° C., followed by centrifugation at 180,000×g for 50 min. The supernatant was removed and discarded. The remaining pellet was homogenized in 20 mM NaCl, 20 mM Tris-HCl, pH 7.4, 1% digitonin and the mixture was incubated at 4° C. for 10 min. Solubilized material was separated as indicated above. This process was repeated a total of five times.

The resulting supernatants ($S_{2-6}$) were pooled, adjusted to 50 mM NaCl and loaded onto a DEAE-Sepharose CL6B column (500 ml of packed gel) equilibrated with 50 mM NaCl, 20 mM Tris-HCl, pH 7.4, 0.1% digitonin. Bound receptor was eluted batchwise with 170 mM NaCl, 20 mM Tris-HCl, pH 7.4, 0.1% digitonin. The eluted ChTX receptor was incubated overnight at 4° C. with 200 ml of WGA-Sepharose in 200 mM NaCl, 20 mM Tris-HCl, pH 7.4, 0.1% digitonin. The suspension was then placed in an empty column, and the fluid phase was collected until the WGA-Sepharose resin was packed. Unbound material was removed by washing with 10 bed volumes of equilibration buffer. Glycoproteins were biospecifically eluted with 200 mM N-acetyl-D-glucosamine in equilibration buffer. The eluate was dialyzed against 20 mM Tris-HCl, pH 7.4, 0.05% digitonin, concentrated 20-fold and adjusted with NaCl to a final concentration of 200 mM. Subsequently, the sample was applied in eight consecutive runs to a Mono Q HR10/10 (Pharmacia) ion exchange column equilibrated with 100 mM NaCl, 20 mM Tris-HCl, pH 7.4, 0.05% digitonin. A linear gradient was applied from 0.1 to 0.5M NaCl over 70 min at a flow rate of 2 ml/min. Fractions displaying ChTX binding activity, between 0.21 and 0.31M NaCl, were adjusted to 80 mM Na-phosphate, pH 7.0 and loaded onto a Bio-Gel HPHT (BioRad) 100×7.8 mm hydroxylapatite column, equilibrated with 80 mM Na-phosphate, pH 7.0, 10 mM NaCl, 0.05% digitonin. Bound material was eluted at a flow rate of 0.5 ml/min with a linear gradient from 80 to 160 mM Na-phosphate in 10 mM NaCl within 12 min, followed by a gradient from 160 mM Na-phosphate in 10 mM NaCl to 560 mM Na-phosphate, 70 mM NaCl within 10 min. Fractions containing ChTX binding activity eluted between 200 and 440 mM Na-phosphate.

The resulting fractions were dialyzed against 20 mM Tris-HCl, pH 7.4, 0.05% digitonin, concentrated, and separated on a continuous 7–25% (w/v) sucrose gradient. Active fractions were dialyzed against 20 mM Mes-NaOH, pH 6.2, 0.05% digitonin and loaded onto a Mono S HR5/5 (Pharmacia) ion exchange column, preequilibrated with the same buffer. Bound material was eluted with a linear gradient from 0 to 700 mM NaCl within 20 min at a flow rate of 0.5 ml/min. Fractions containing ChTX binding activity, which eluted between 120 and 260 mM NaCl, were dialyzed against 20 mM Tris-HCl, pH 7.4, 0.01% digitonin, concentrated to 0.3 ml and applied to another continuous sucrose gradient as described above. Using this purification scheme, the ChTX receptor was purified almost 2000-fold with recovery of 3.3% of the initial binding activity. Total recoveries at each individual step during purification are close to 100% indicating that no significant loss of activity occurs during the time involved in the purification procedures.

Fractions from the last sucrose density gradient centrifugation containing 31–158 ng of protein were dialyzed against 10 mM Na-borate, pH 9.0, 0.05% Triton X-100 and then reacted with 3.5 mCi of [$^{125}$I]Bolton-Hunter reagent (2200 Ci/mmol; New England Nuclear Corporation) for 15 min on ice. The reaction was quenched by addition of Tris-HCl, pH 7.4 to a final concentration of 100 mM. Covalent incorporation of [$^{125}$I]ChTX into the purified receptor was accomplished with the bifunctional reagent, disuccinimidyl suberate as previously described for crosslinking ChTX to its receptor in membranes (Garcia-Calvo, M., Vazquez, J., Smith, M., Kaczorowski, G. J., and Garcia, M. L. (1991) Biochemistry 30, 11157–11164). Briefly, the purified receptor preparation was incubated with 130 pM [$^{125}$I]ChTX in 10 mM NaCl, 10 mM Taps-NaOH, pH 9.0, 0.1% digitonin, in the absence or presence of unlabeled ChTX, for two hours at room temperature. The solution was then adjusted to 0.2M NaCl and disuccinimidyl suberate was added to a final concentration of 0.18 mM. After incubation at room temperature for 1 min, the reaction was stopped by addition of Tris-HCl, pH 7.4 to a final concentration of 200 mM. Samples were dialyzed against 10 mM Tris-HCl, pH 7.4, 0.05% digitonin, concentrated 10 fold, and subjected to SDS-PAGE. Samples were resuspended into SDS-PAGE sample buffer containing 1% β-mercaptoethanol or 50 mM DTT and incubated at 37° C. for 120 min. Samples were subjected to SDS-PAGE using either continuous or discontinuous acrylamide gels (Laemmli, U. K. (1970) Nature 227, 680–685), and dried gels were exposed to Kodak XAR-5 film.

The purified ChTX receptor migrated in sucrose gradients as a large particle with an apparent sedimentation coefficient of 23S. When fractions from the sucrose gradient were subjected to SDS-PAGE, staining with silver revealed a single component with an apparent molecular weight of 62,000 that comigrated with [$^{125}$I]ChTX binding activity. A component of 31,000 was specifically labeled with [125I] ChTX in the presence of disuccinimidyl suberate. Labeling of this protein is abolished by agents such as IbTX, TEA and potassium that are known to inhibit ChTX binding to maxi-K channels. Since this component is heavily glycosylated, it does not stain well by conventional protein staining techniques. Therefore, fractions from the sucrose gradient were labeled with [$^{125}$I]Bolton-Hunter reagent, subjected to SDS-PAGE and analyzed by autoradiography. From the distribution of [$^{125}$I]Bolton-Hunter labeled polypeptides, it is evident that ChTX binding activity correlates with the presence of two subunits, α and β, of 62,000 and 31,000 apparent molecular weights.

The relationship between the β subunit identified after Bolton-Hunter labeling of the purified preparation and the component labeled with [$^{125}$I]ChTX in crosslinking experiments was further examined. Deglycosylation experiments were carried out with both preparations. Samples were dialyzed for 12 hours at 4° C. against 5 mM Tris-HCl, pH 7.4, 0.05% digitonin and denatured by heating for 5 min at 65° C. in the presence of 0.5% SDS, 50 mM β-mercaptoethanol. Samples were adjusted to 1.3% Nonident P-40 (w/v), and deglycosylation was started by addition of 1 IU recombinant N-glyconase F (Genzyme). After incubation at 37° C. for different periods of time, the reaction was stopped by addition of boiling SDS sample buffer, samples were subjected to SDS-PAGE and dried gels were exposed to Kodak XAR-5 film. Recombinant N-glycanase caused a time-dependent conversion of the [$^{125}$I]ChTX crosslinked protein (apparent molecular weight of 35,000; 31 kDa for the core protein plus 4.4 kDa contributed by the radiolabeled toxin) into an intermediate form of 28.9 kDa and a final product of 25.6 kDa. These experiments indicate that this protein is heavily glycosylated, most probably at two different glycosylation sites by N-linked sugars. The same experiment was repeated with purified [$^{125}$I]Bolton-Hunter labeled receptor. The β subunit displayed an identical time-course of deglycosylation to that of the [$^{125}$I]ChTX crosslinked protein. The apparent molecular weight of the deglycosylated [$^{125}$I] Bolton-Hunter labeled core protein was determined independently by Ferguson plot analysis (Frank, R. N., and Rodbard, D. (1975) Arch. Biochem. Biophys. 171, 1–13) to be 21.4 kDa. This molecular weight is in good agreement with the value obtained after deglycosylation of the [$^{125}$I] ChTX labeled subunit if 4.4 kDa contributed by the radiolabeled toxin is subtracted from the mass of the final product.

EXAMPLE 2

Sequencing Peptides Derived from the Purified β Subunit

Fractions from the final sucrose density gradient centrifugation of the ChTX receptor purification, containing ~31 pmoles of [$^{125}$I]ChTX binding sites, were dialyzed against 10 mM sodium borate, pH 8.8, 0.05% Triton X-100, and reacted with 50 μCi [$^{125}$I]Bolton-Hunter labeling reagent (2200 Ci/mmol) for 15 min on ice. The iodinated sample was separated by electrophoresis on a 12% SDS-polyacrylamide gel and the wet gel exposed for 30 min to Kodak XAR film. The area of radioactivity corresponding to the location of the β subunit (and a control area) were cut from the gel and electroeluted for 12 hours in 0.1M ammonium acetate, 0.1% SDS. The sample was dialyzed against 40 mM sodium phosphate, pH 7.8, 0.02% SDS for 24 hours, concentrated 5 fold, and then incubated with 5 μg of V$_8$ endoproteinase Glu-C (final concentration of 100 μg/ml) for 14 hours at room temperature. The digested β subunit was loaded onto a Vydac C$_4$ column (RP-300, 5 μm, 150×2.1 mm), equilibrated with 2% acetonitrile and 10 mM TFA, using an ABI 130A separation system. Elution was achieved in the presence of a linear gradient from 2–99% acetonitrile at a flow rate of 50 μL/min. The collected peptides were loaded onto Porton peptide filter supports and subjected to automated Edman degradation employing an integrated microsequencing system (Porton Instruments PI2090E) with an on-line detection system. The sequence of a 28 amino acid peptide derived from the β subunit was obtained using these procedures. The sequence is as follows:

GKKLVMAQCLGETRALCLGVAMVVGAVI

EXAMPLE 3

Molecular Cloning of the β Subunit

Based on the sequence obtained from the β subunit, degenerate oligonucleotides encoding amino acid residues 2–7 and 20–24 of the peptide were synthesized and used as primers in PCR. cDNA was synthesized from bovine tracheal smooth muscle poly A+mRNA (using the degenerate oligo encoding residues 20–24 as the primer) and this cDNA was used as the template in the PCR. [α-32P]dATP (100

μCi/ml) was added to the reaction to label the products and the solution was cycled 25 times at 94° C., 37° C., and 72° C. for 1, 2, and 3 min, respectively. The amplified product was fractionated on a 6% DNA sequencing gel and the region of the gel surrounding the cDNA of the expected length (from 82–92 bp; based on the peptide sequence) was excised. The DNA was eluted into 0.5 ml $H_2O$ (22° C., 60 min) and 30 μl of the eluted cDNA were reamplified using 50 cycles of the PCR as described above, but without [$^{32}P$]dATP. The product of this PCR reaction was cloned and sequenced by standard techniques. An unambiguous 41 bp fragment encoding the peptide sequence MAQRRGE-TRALCLG was thereby determined. An oligonucleotide probe encoding these 41 bp was constructed, labeled (>$10^8$ cpm/pmol), and used to probe Northern blots and screen cDNA libraries.

A λgt10 cDNA library was constructed from bovine aortic smooth muscle poly (A+) mRNA and screened with the 41 bp oligonucleotide probe. Viruses were plated on *E. coli*, C600 hfl at a density of 40,000 pfu/135 mm plate. After plaque formation, phage from 36 plates were transferred to Hybond-N filters and hybridized to the probe (2 pmole) overnight at 42° C. in a buffer containing 5×saline/sodium phosphate/EDTA, 0.5% SDS, 5×Denhardt's solution. Filters were washed to a final stringency of 0.1×SSC/0.1% SDS at 65° C. Five phage containing cDNAs that hybridized to the probe were isolated in this manner. The cDNA from each was excised from the viral DNA by digestion with Not I and subcloned into pKSII+. The longest was sequenced on both strands by the dideoxynucleotide termination method. A bovine tracheal cDNA encoding the β subunit was subsequently isolated by PCR using primers derived from the sequence of the aortic cDNA clone and bovine tracheal cDNA as the template. The nucleotide sequences of the cDNAs from both tissues were identical. Northern blot analysis of poly A+mRNAs, isolated from either bovine tracheal or aortic smooth muscles, demonstrated that the cDNA hybridized to mRNAs of the same sizes in each tissue. Thus, strong hybridization to a transcript of ~3.8 kb and weaker hybridization to one of ~1.7 kb was observed in blots of RNAs from both tissues. The pattern of hybridization was identical in blots probed with a cDNA encoding the entire open reading frame of the protein or with a 41 bp oligonucleotide encoding only amino acids 7–20 in the sequence.

The cDNAs encode a protein of 191 amino acids with a molecular weight of 21,957 Da, consistent with the size of the deglycosylated protein in purified preparations of the channel. The deduced sequence of the protein is unique, bearing little sequence or structural homology to subunits of other known ion channels. Hydropathy analysis demonstrated the presence of two hydrophobic, putative transmembrane, domains in the protein. There are three potential sites for N-linked glycosylation and one consensus sequence for phosphorylation by protein kinase A. With the absence of a canonical signal sequence and the presence of two strongly hydrophobic regions, it is likely that the protein has intracellular amino and carboxy termini and one large extracellular domain. This topology would place two of the potential N-glycosylation sites in the extracellular space, consistent with biochemical evidence suggesting the presence of two N-linked sugar moieties attached to the protein. Furthermore, in this orientation, the cAMP-dependent protein kinase recognition sequence would be located in the cytoplasm, also consistent with published reports of PKA modulation of maxi-K currents (Reinhart, P. H., Chung, S., Martin, B. L., Brautigan, D. L., and Levitan, I. B. (1991) *J. Neurosci.* 11, 1627–35; Chung, S. K., Reinhart, P. H., Martin, B. L., Brautigan, D., and Levitan, I. B. (1991) *Science* 253, 560–62). There are three Lys residues in the putative extracellular domain. One (or more) of these residues is expected to be the site for covalent attachment of [$^{125}I$]ChTX in the presence of the bifunctional crosslinking reagent, disuccinimidyl suberate. The peptide sequence, determined from a fragment derived from an *S. aureus* $V_8$ protease digestion, begins at $Gly_2$ in the deduced sequence. Since this enzyme cleaves proteins specifically after Glu or Asp residues, and in the sequence deduced from the cDNA, $Gly_2$ follows the putative initiator Met residue, the amino terminus of the protein may be processed post-translationally to remove the methionine. The overall structure of the protein deduced from the cDNA sequence corresponds well to the biochemical properties of the purified protein which strongly supports the idea that it represents the β subunit of the maxi-K channel.

EXAMPLE 4
Production of Antibodies Against the β Subunit

Site-directed rabbit antisera were produced against two domains of the putative extracellular loop of the β subunit protein using techniques described previously (Knaus H.-G., Garcia-Calvo, M., Kaczorowski, G. J., and Garcia, M. L. (1994) *J. Biol. Chem* 269, 3921–3924). The sequences of these peptides are DQEELEGKRVPQYP (anti-β61–75) and ADVEKVRARFHENQD (anti-β118–132). For all immunoprecipitation studies, anti-β antibodies were prebound to Protein-A Sepharose 4B as described (Knaus H.-G., Garcia-Calvo, M., Kaczorowski, G. J., and Garcia, M. L. (1994) *J. Biol. Chem* 269, 3921–3924). The gel was washed three times with 1 mL of RIA buffer (150 mM NaCl, 20 mM Tris-HCl, pH 7.4, 1% Triton X-100, 1 mg/ml bovine serum albumin) before the addition of either the isolated [$^{125}I$] Bolton-Hunter labelled β subunit, the [$^{125}I$]ChTX-crosslinked β subunit, or the $^{125}I$-labelled, native maxi-K channel complex (containing both the α and β subunits). In all preparations that had been denatured by boiling in SDS in the presence of β-mercaptoethanol, the final SDS concentration was never allowed to exceed 0.05%. The immunoprecipitated samples were analyzed by SDS-PAGE after denaturation of the resin for 15 min at 56° C. in SDS sample buffer containing 1% β-mercaptoethanol. Gels were dried and exposed to Kodak XAR film at −80° C.

Under denaturing conditions, the site-directed antibodies raised against two putative extracellular epitopes of the β subunit specifically immunoprecipitated the [$^{125}I$]Bolton-Hunter labelled β subunit, as well as the [125I]ChTX crosslinked β subunit. In addition, these sera recognized the 31 kDa protein on Western blots of purified maxi-K channel preparations. Immunoreactivity paralleled ChTX binding throughout the fractions of the last sucrose density gradient in the purification procedure. Under nondenaturing conditions, however, these anti-β sera immunoprecipitated both the α and β subunits of the channel. These data provide independent immunological evidence that the protein encoded by the cDNA does, in fact, represent the β subunit of the maxi-K channel and that, in vivo, the channel exists as a tight complex of both the α and β subunits.

EXAMPLE 5
Coexpression of the β-Subunit with the α-Subunit cDNAs encoding both the α and β subunits were used as templates for the production of cRNA. The α subunit cDNA was obtained from Leo Pallanck (Univ. of Wisconsin) and consisted of a full-length mouse brain cDNA (mslo19; GenBank Accession #U09383) in an RNA transcription vector, pGH. The mslo19 cDNA was cloned by hybridization using a fragment of the Drosophila slowpoke cDNA, and is nearly identical to a published sequence, mbr5, encoding a large conductance, $Ca^{2+}$-activated potassium channel α subunit (A. Butler, S. Tsunoda, D. P. McCobb, A. Wei, and L. Salkoff, *Science* 261: 221–224), and probably represents a splice variant from the same gene. cRNA transcribed from the mslo 19 cDNA did not produce potassium channels in Xenopus oocytes. We therefore used standard techniques to modify the mslo19 cDNA, specifically by deleting the 5' non-coding sequence (bases 1 to 940), and replacing that sequence with a consensus eukaryotic translation initiation sequence: 5'-GCCGCCACC-3'. This modified construct (mslo19 Δ5'UTR) contained the identical open reading frame as the original mslo19 cDNA and proved to be a good template for production of cRNA encoding the α-subunit of a large-conductance, calcium activated potassium channel, as explained below. A fragment of the β subunit cDNA, including the entire open reading frame, was subcloned into a pGEM (Promega, inc.) vector for cRNA transcription. The cRNAs encoding both the α and β subunits were transcribed using the appropriate RNA polymerase as determined by the transcription vector (T7 for α, and SP6 for β) and capped in vitro using a kit (mCAP; Stratagene, inc), purified by size-exclusion chromatography using sepahadex G-50 spin columns (Bio-Rad, inc.), and analyzed for purity and length by agarose/formaldehyde gel electrophoresis according to established procedures. Following ethanol precipitation, cRNAs were resuspended in sterile, DEPC-treated water at a concentration of 0.1 to 1 µg/µl, and stored in 2 µl aliquots at −8° C.

Injection of mRNA or cRNA into Xenopus oocytes was done by a modification of established protocols (A. Coleman, *Transcription and Translation: A Practical Approach*. B. D. Hanes, S. J. Higgins, Eds., 1984); Y. Masu, et al., *Nature* 329, 836–838 (1987)). Oocytes were surgically removed from 0.17% tricaine anesthetized *Xenopus laevis* (Xenopus One). The excised ovarian lobes were teased apart with jeweler's forceps and then placed into OR-2 (82.5 mM NaCl, 2 mM KCl, 1 mM $MgCl_2$, 5 mM HEPES, pH 7.4) containing 2 mg/ml collagenase β (Boehringer Mannhiem) for 2 hours at room temperature with a change of the buffer at 1 hour. Isolated oocytes were repeatedly washed in OR-2 until the supernatant remained clear. Stage 5 and 6 oocytes were selected and cultured overnight in supplemented OR-2 (OR-2 containing 1.8 mM $CaCl_2$ and 0.5 mg/ml gentamycin. Oocytes were injected with 46 nl of RNA at a concentration of 0.1 to 1.0 mg/ml in $H_2O$. RNA was injected using a Nanoject automatic oocyte injector (Drummond Scientific) and injection needles were pulled from 3.5" Drummond capillaries using a Micropipette puller (Kopf Instruments).

Currents were recorded from Xenopus oocytes using two-electrode voltage-clamp methods to record currents from the entire oocyte and patch-clamp methods to record current from small patches of membrane excised from the oocytes. Recordings were done at room temperature and were performed 1 to 30 days after injection.

Oocytes having been previously injected with cRNAS encoding either α-subunit or β-subunit or both subunits together, were transferred to a plastic recording chamber by means of a fire-polished pasteur pipet. The chamber contained ND-96 saline (96 mM NaCl, 5 mM KCl, 1 mM $MgCl_2$, 1.8 mM $CaCl_2$, 10 mM Na-HEPES, pH 7.3). Microelectrodes having resistances of 0.2 to 1 Mohm when filled with 1M KCl were fashioned using a Narashige pipete puller from DAGAN LE-16 glass capillary tubes. KCl-filled electrodes were attached using the manufacturer's -supplied holders to a DAGAN CA-1 oocyte voltage clamp. Using appropriate micromanipulators, and following procedures as outlined in the operator's manual for the CA-1 voltage clamp, the oocyte was impaled by two electrodes, and recordings of membrane currents were obtained from the oocytes expressing either α-subunit or β-subunit or both subunits together. Recordings were obtained at room temperature. Stimulus protocols, in the form of rectangular voltage pulses, or voltage ramps, were presented to the voltage-clamped oocyte with the aid of a computer-based data acquisition system (PClamp; Axon Instruments), and the currents so elicited were stored as electronic data files for subsequent retrieval and analysis.

Patch clamp recordings were made from membrane patches excised from Xenopus oocytes that had their vitilin membranes removed using conventional techniques (Hamill, O. P., Marty, A., Neher, E., Sakmann, B., and Sigworth F. J. *P fluegers Arch.* 391, 85–100 (1991)) at room temperature. Glass capillary tubing (Garner #7052) was pulled in two stages to yield micropipettes with tip diameters of approximately 1–2 microns. Pipettes were typically filled with solutions containing (mM): 150 KCl, 10 Hepes (4-(2-hydroxyethyl)-1-piperazineethanesulfonic acid), 0.01 Ca, and adjusted to pH 7.20 with 3.7 mM KOH. After forming a high resistance ($>10^9$ ohms) seal between the plasma membrane and the pipette, the pipette was withdrawn from the cell forming an excised inside-out membrane patch. The patch was excised into a bath solution containing (mM): 150 KCl, 10 Hepes, 0.001 to 0.1 Ca, and the pH was adjusted to 7.2 with 3.7 KOH. An Axopatch 1C amplifier (Axon Instruments, Foster City, Calif.) with a CV-4 headstage or a List EPC-7 amplifier was used to control the voltage and to measure the currents flowing across the membrane patch. The input to the headstage was connected to the pipette solution with a Ag/AgCl wire, and the amplifier ground was connected to the bath solution with a Ag/AgCl wire via a bridge containing agar dissolved in 0.2M KCl. Maxi-K channels were identified by their large single channel conductance (>200 pS) and sensitivity of channel open probability to membrane potential and intracellular calcium concentration.

Data were stored on a Racal store 4DS FM tape recorder (Racal Recorders, Vienna, Va.) or on digital video tape using a video casette recorder after digitizing the signal with VR-10 (Instrutech Corp., Belmont N.Y.) PCM video encoder. For quantitative analysis, the data were played into a DEC 11-73 (Digital Equipment Corp., Maynard, Mass.) after digitization with a DT2782-8D1A analogue to digital converter (Data Translation Inc., Marlboro, Mass.), or played into a Mac IIx or Quadra 700 or Quadra 950 computer (Apple Computers) after digitization with an ITC-16 interface (Instrutech Corp., Belmont, N.Y.).

Oocytes injected with cRNA encoding the β subunit alone exhibited no measurable potassium currents different from currents seen in control, uninjected oocytes using both the whole-oocyte and patch-clamp recording techniques. Oocytes injected with cRNA encoding the α subunit alone exhibited large (>5 µA) outward currents in whole-oocyte voltage-clamp experiments that were activated at positive membrane potentials. These outward currents were blocked by ChTX and IbTX at 10 to 30 nM. Patch-clamp recordings were made from excised, inside-out membrane patches obtained from these oocytes. In patches with a low density of channels (1–10 channels per patch), individual maxi-K channels could be distinguished with a large single-channel conductance (>200 pS). The open probability of these channels was increased by increasing the intracellular concentration of calcium or by increasing the membrane potential. When the density of channels in the oocytes increased, and the patches contained many channels (>50), then the steps in current due to opening and closing of individual channels could not be distinguished. Since these patches contained many channels, the stochastic variations in open probability of individual channels was averaged out, and accurate measures of the effects of intracellular calcium, membrane potential and drugs could be obtained from each individual patch. In these macroscopic patch recordings, channel open probability was determined from patch conductance, and increased smoothly as a function of membrane potential until the maximal conductance was achieved. Channel open probability showed an e-fold increase per 15–25 mV increase in membrane potential. The midpoint of the conductance-voltage curves was shifted in the hyperpolarizing direction by increasing intracellular calcium concentrations. The currents flowing through these channels was selective for potassium over sodium or chloride because no appreciable outward currents were observed when the intracellular solution was changed from 150 mM KCl to 150 mM NaCl. The currents in these patches were not increased by 100–500 nM of dehydrosoyasaponin I (DHS-I), a potent activator of maxi-K channels in some smooth muscle tissues (McManus O. B., Harris, G. H., Giangiacomo, K. M., Feigenbaum, P., Reuben, J. P., Addy, M. E., Burka, J. F., Kaczorowski, G. J., and Garcia, M. L. *Biochemistry* 32, 6128–33 (1993).

Oocytes injected with cRNAs encoding both the α and β subunits exhibited outward potassium currents in two-electrode voltage clamp recordings of the entire oocyte that were blocked by ChTX and IbTX. The magnitudes of currents recorded from oocytes that were injected with cRNAs encoding both the α and β subunits were similar to the currents observed in oocytes injected with cRNA encoding the α subunit alone. The outward currents observed in the oocytes injected with α and β subunits were activated at more negative potentials than the oocytes injected with α subunit cRNA alone. Direct evidence for a difference in channel gating between channels in oocytes injected with cRNA encoding α subunit alone and channels in oocytes injected with cRNAs encoding both the α and β subunits comes from recordings of currents in membrane patches excised (inside-out configuration) from each type of oocyte. Maxi-K channels observed in α and β subunit-injected oocytes had a large single channel conductance (>200 pS), and these channels were selective for potassium over sodium. The open probability of these channels was increased by increasing intracellular calcium concentrations and by membrane depolarization. The gating of the channels in oocytes injected with both α and β subunit cRNAs differed from the gating of channels from oocytes injected with α subunit cRNA alone. The channels from oocytes expressing both subunits were activated at more negative membrane potentials than were channels expressing the α subunit alone. At a given concentration of intracellular calcium, channels from oocytes expressing both subunits were activated at membrane potentials 50 to 100 mV more negative than were channels from oocytes expressing the α subunit alone. The shift in the voltage-dependence of gating of channels due to coexpression of the β subunit was similar to the shift in voltage-dependence of channel gating that occurs after a ten-fold increase in intracellular calcium concentration. Channels from oocytes expressing both subunits were fully activated by 100–300 nM of DHS-I applied to the intracellular face of the channel. Thus, addition of the β subunit shifted the voltage-dependence of gating of channels encoded by the α subunit, and conferred sensitivity to an activator of maxi-K channels. Therefore, the β subunit co-assembles with the α subunit and forms calcium-activated potassium channels with pharmacological and biophysical properties that differ from calcium-activated potassium channels encoded by the α subunit alone.

EXAMPLE 6

Cloning of β Subunit cDNA into Vectors for Expression in Insect Cells

Baculovirus vectors, which are derived from the genome of the AcNPV virus, are designed to provide high level expression of cDNA in the Sf9 line of insect cells (ATCC CRL#1711). Recombinant baculoviruses expressing β subunit cDNA is produced by the following standard methods (In Vitrogen Maxbac Manual): the β subunit cDNA constructs are ligated into the polyhedrin gene in a variety of baculovirus transfer vectors, including the pAC360 and the BlueBac vector (In Vitrogen). Recombinant baculoviruses are generated by homologous recombination following co-transfection of the baculovirus transfer vector and linearized AcNPV genomic DNA [Kitts, P. A., *Nuc. Acid. Res.* 18, 5667 (1990)] into Sf9 cells that may also be expressing the α subunit. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, β subunit expression is measured by the assays described herein.

The cDNA encoding the entire open reading frame for β subunit is inserted into the BamHI site of pBlueBacII. Constructs in the positive orientation are identified by sequence analysis and used to transfect Sf9 cells that may also be expressing the α subunit in the presence of linear AcNPV wild type DNA.

Authentic, active β subunit is found in association with the infected cells. Active β subunit or α-β heteromultimers are extracted from infected cells by hypotonic or detergent lysis.

Alternatively, the human β subunit receptor is expressed in the Drosophila Schneider 2 cell line that may also be expressing the α subunit by cotransfection of the Schneider 2 cells with a vector containing the β subunit DNA downstream and under control of an inducible metallothionin promoter, and a vector encoding the G418 resistant neomycin gene. Following growth in the presence of G418, resistant cells are obtained and induced to express β subunit by the addition of $CuSO_4$. Identification of modulators of the β subunit or the maxi-K channel is accomplished by assays using either whole cells or membrane preparations.

EXAMPLE 7

Cloning of β Subunit cDNA into a Yeast Expression Vector

Recombinant β subunit is produced in the yeast *S. cerevisiae* that may also be expressing the α subunit following the insertion of the optimal β subunit cDNA cistron into expression vectors designed to direct the intracellular or extracellular expression of heterologous proteins. In the case of intracellular expression, vectors such as EmBLyex4 or the like are ligated to the β subunit cistron [Rinas, U. et al., *Biotechnology* 8, 543–545 (1990); Horowitz B. et al., *J. Biol. Chem.* 265, 4189–4192 (1989)]. For extracellular expression, the β subunit cistron is ligated into yeast expression vectors which fuse a secretion signal. The levels of expressed β subunit or maxi-K channels are determined by the assays described herein.

EXAMPLE 8
Purification of Recombinant β Subunit and α-β Heteromultimers

Recombinantly produced β subunit or maxi-K channels may be purified by antibody affinity chromatography.

β subunit antibody affinity columns are made by adding the anti-β subunit antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents (e.g., 0.1% digitonin) and the cell culture supernatants or cell extracts containing solubilized β subunit or the α-β subunit heretomultimer are slowly passed through the column. The column is then washed with phosphate-buffered saline together with detergents until the optical density (A280) falls to background, then the protein is eluted with 0.23M glycine-HCl (pH 2.6) together with detergents. The purified β subunit protein or maxi-K channel is then dialyzed against phosphate buffered saline containing appropriate detergents.

What is claimed is:

1. An isolated and purified nucleic acid molecule comprising a nucleotide sequence encoding a native bovine maxi-K potassium channel β-subunit polypeptide, wherein the nucleotide sequence is not directly linked to the sequences which adjoin the corresponding gene in native bovine genomic DNA, and wherein the polypeptide specifically binds to a monoclonal antibody which specifically binds to the maxi-K β-subunit polypeptide having the amino acid sequence shown in SEQ ID NO: 2.

2. An isolated and purified nucleic acid molecule which encodes the amino acid sequence of a maxi-K potassium channel β-subunit polypeptide shown in SEQ ID NO: 2, wherein the nucleotide sequence is not directly linked to the sequences which adjoin the corresponding gene in native bovine genomic DNA.

3. A nucleic acid molecule according to claim 2, comprising the nucleotide sequence of a cDNA molecule.

4. A nucleic acid molecule according to claim 2, comprising the nucleotide sequence of a cRNA molecule.

5. A nucleic acid molecule according to claim 2, comprising the nucleotide sequence shown in SEQ ID NO: 1.

6. A nucleic acid molecule according to claim 2, comprising the nucleotide sequence of a genomic DNA clone.

7. An expression vector comprising the nucleotide sequence of a nucleic acid molecule according to claim 2.

8. An expression vector comprising the nucleotide sequence of a nucleic acid molecule according to claim 6.

9. A cultured host cell containing nucleic acid which comprises the nucleotide sequence of a nucleic acid molecule according to claim 2.

10. A cultured host cell containing nucleic acid which comprises the nucleotide sequence of a nucleic acid molecule according to claim 6.

11. A process for expressing a maxi-K β subunit polypeptide, comprising the steps of:

introducing a nucleic acid molecule according to claim 2 into a suitable host cell; and culturing the host cell under conditions which allow expression of the β subunit polypeptide encoded by the nucleic acid molecule.

12. A process for expressing a maxi-K β subunit polypeptide, comprising the steps of:

introducing an expression vector according to claim 7 into a suitable host cell; and culturing the host cell under conditions which allow expression of the β subunit polypeptide encoded by the vector.

13. An isolated and purified nucleic acid molecule comprising a nucleotide sequence encoding a native human maxi-K potassium channel β-subunit polypeptide, wherein the nucleotide sequence is not directly linked to the sequences which adjoin the corresponding gene in native human genomic DNA, and wherein the polypeptide specifically binds to a monoclonal antibody which specifically binds to the maxi-K β-subunit polypeptide having the amino acid sequence shown in SEQ ID NO: 4.

14. An isolated and purified nucleic acid molecule which encodes the amino acid sequence of a maxi-K potassium channel β-subunit polypeptide shown in SEQ ID NO: 4, wherein the nucleotide sequence is not directly linked to the sequences which adjoin the corresponding gene in native human genomic DNA.

15. A nucleic acid molecule according to claim 14, comprising the nucleotide sequence of a cDNA molecule.

16. A nucleic acid molecule according to claim 14, comprising the nucleotide sequence of a cRNA molecule.

17. A nucleic acid molecule according to claim 14, comprising the nucleotide sequence shown in SEQ ID NO: 3.

18. A nucleic acid molecule according to claim 14, comprising the nucleotide sequence of a genomic DNA clone.

19. An expression vector comprising the nucleotide sequence of a nucleic acid molecule according to claim 14.

20. An expression vector comprising the nucleotide sequence of a nucleic acid molecule according to claim 18.

21. A cultured host cell containing nucleic acid which comprises the nucleotide sequence of a nucleic acid molecule according to claim 14.

22. A cultured host cell containing nucleic acid which comprises the nucleotide sequence of a nucleic acid molecule according to claim 18.

23. A process for expressing a maxi-K β subunit polypeptide, comprising the steps of:

introducing a nucleic acid molecule according to claim 14 into a suitable host cell; and culturing the host cell under conditions which allow expression of the β subunit polypeptide encoded by the nucleic acid molecule.

24. A process for expressing a maxi-K β subunit polypeptide, comprising the steps of:

introducing an expression vector according to claim 19 into a suitable host cell; and culturing the host cell under conditions which allow expression of the β subunit polypeptide encoded by the vector.

* * * * *